US00RE34878E

United States Patent [19]

Toyoshima et al.

[11] E Patent Number: Re. 34,878

[45] Reissued Date of Patent: Mar. 14, 1995

[54] HYPOGLYCEMIC AGENT

[75] Inventors: Shigeshi Toyoshima; Yoshiko Seto, both of Funabashi; Hisashi Shinkai, Kawasaka; Koji Toi, Kanagawa; Izumi Kamashiro, Yokohama, all of Japan

[73] Assignee: Ajinomoto Co., Inc., Tokyo, Japan

[21] Appl. No.: 157,564

[22] Filed: Nov. 23, 1993

Related U.S. Patent Documents

Reissue of:

[64] Patent No.: 4,816,484
Issued: Mar. 28, 1989
Appl. No.: 146,719
Filed: Jan. 21, 1988

U.S. Applications:

[62] Division of Ser. No. 844,970, Mar. 27, 1989, abandoned.

[30] Foreign Application Priority Data

Mar. 27, 1985 [JP] Japan ..... 60-62276

[51] Int. Cl.[6] ..... A61K 31/215; C07C 101/72

[52] U.S. Cl. ..... 514/563; 514/529; 514/530; 549/304; 549/467; 546/169; 546/323; 560/40; 560/41; 562/445; 562/450

[58] Field of Search ..... 562/445; 560/40; 514/563, 613

[56] References Cited

U.S. PATENT DOCUMENTS 4,650,785 3/1987 Toyoshima et al. .
4,670,584 6/1987 Toyoshima et al. .

FOREIGN PATENT DOCUMENTS 93551 9/1983 European Pat. Off. .
2102412 2/1983 United Kingdom .

OTHER PUBLICATIONS

Toyoshima et al., "Preparation of D-Phenylalanine Derivatives and Their Use as Hypoglycemic Agents", CA 106 85057d (1987).

European Search Report/Application No. 86 30 2217/26-11-1987.

*Primary Examiner*—C. Warren Ivy
*Assistant Examiner*—A. A. Owens
*Attorney, Agent, or Firm*—Oblon, Spivak, McClelland, Maier & Neustadt

[57] ABSTRACT

A compound of D-phenylalanine derivative for hypoglycemic use, represented by the general formula

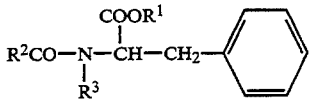

$R^1$ is selected from hydrogen, alkyl of 1 to 5 carbon atoms, aryl of 6 to 12 carbon atoms, aralkyl of 6 to 12 carbon atoms,

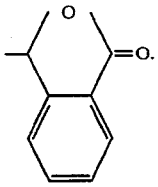

$—CH_2CO_2R^3$, $—CH(CH_3)—OCO—R^3$, and $—CH_2—OCO—C(CH_3)_3$; $R^2$ is selected from groups comprising aryl of 6 to 12 carbon atoms, a hetero six-membered ring, a hetero five-membered ring, cycloalkyl, or cycloalkenyl, any of which groups may have one or more substituents; and $R^3$ is selected from hydrogen and alkyl of 1 to 5 carbon atoms; the salts thereof, and precursors which can be converted thereto in the human or animal body.

Some of the compounds are novel per se.

16 Claims, No Drawings

HYPOGLYCEMIC AGENT

Matter enclosed in heavy brackets [ ] appears in the original patent but forms no part of this reissue specification; matter printed in italics indicates the additions made by reissue.

This application *is a Reissue of Ser. No. 07/146,719, filed Feb. 21, 1988, U.S. Pat. No. 4,816,182, which is a* divisional of Ser. No. 844,970, filed Mar. 27, 1986, now abandoned.

FIELD OF THE INVENTION

The present invention relates to hypoglycemic agents useful as antidiabetic drugs.

BACKGROUND TO THE INVENTION

Hitherto, as antidiabetic drugs for oral use, there have been widely employed sulfonyl urea which shows hypoglycemic action particularly through a promotion of the secretion of insulin, and a biguanide which shows a hypoglycemic action particularly through the metabolism of sugar. However, they are somewhat unsatisfactory as to their side effects (see Textbook of Endocrinology 4th ed., 1968, p. 719 (Saunders); Diabetes, 19, 785, 1970; Ann. Rev. Pharmacol., 15, 351, 1975).

No report has ben found that a D-phenylalanine derivative possesses hypoglycemic action.

SUMMARY OF THE INVENTION AND DESCRIPTION OF PREFERRED EMBODIMENTS

According to one aspect of the invention there is provided for pharmaceutical, particularly hypoglycemic, use, a D-phenylalanine derivative represented by the general formula:

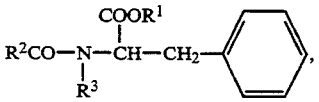

(I)

or a salt thereof, or a precursor which can be converted thereto in the human or animal body. Such compounds can lower the value of blood sugar and thus can be used as an antidiabetic drug for an oral use as well as by injection.

Among the foregoing phenylalanine derivatives, those in the D-form represented by the general formula:

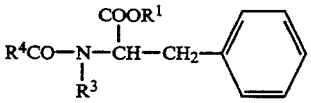

and the salts thereof are novel.

In the above general formulae: $R^1$ is hydrogen, alkyl of 1 to 5 carbon atoms such as methyl, ethyl, n-propyl, isopropyl, n-butyl, and sec-butyl, aryl of 6 to 12 carbon atoms such as phenyl, tolyl, naphthyl, and

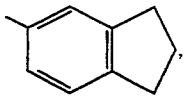

aralkyl of 6 to 12 atoms such as benzyl,

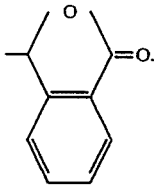

$—CH_2CO_2R^3$, $—CH(CH_3)—OCO—R^3$, or $—CH_2—OCO—C(CH_3)_3$, $R^2$ is a group comprising aryl of 6 to 12 carbon atoms such as phenyl, naphthyl, and indanyl, a hetero six-membered ring such as quinolynyl, pyridyl, a hetero five-membered ring such as 2-benzofuranyl, cycloalkyl such as cyclohexyl and cyclopentyl, bicycloalkyl such as bicycloheptye, and cycloalkenyl such as 1-cyclohexenyl, 2-cyclohexeneyl, 3-cyclohexenyl, 1-cyclopentenyl and 2-cyclopentenyl, any of which groups optionally having one or more substituents; $R^3$ is hydrogen or lower alkyl such as methyl, ethyl, isopropyl and pentyl; and $R^4$ stands for those $R^2$ groups which provide novel compounds hereof, notably phenyl which has one or more alkyl substituents of 2 to 5 carbon atoms, cyclohexyl which has one or more substituents cyclopentyl, bicycloalkyl, cycloalkenyl, indanyl or 2-benzofuranyl, any of which may have one or more substituents.

When an organic group in the above general formulae has a substituent, examples of such substituents include a halogen atom such as fluorine or chlorine, a hydroxyl group, a $C_{1-5}$ alkyl group such as methyl, ethyl, trichloromethyl, trifluoromethyl, propyl, isopropyl, n-butyl, sec-butyl, and tert-butyl, a $C_{1-5}$ alkenyl group such as ethenyl, propenyl, and butenyl, an alkylidene group such as

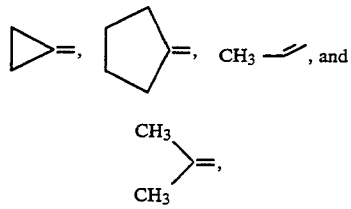

a $C_{1-5}$ alkyloxy such as methoxy and ethoxy, a $C_{1-5}$ alkyl group which has been substituted by such $C_{1-5}$ alkyloxy group such as methoxymethyl and 1-ethoxyethyl, a $C_{1-5}$ alkylene group which has been substituted by such $C_{1-5}$ alkyloxy group in the same manner as above such as 1-methoxyethylene. In the case of a substituted bicycloalkyl group as stated above, it can include a bicycloheptyl or a derivative thereof such as bicyclo (2,2,1)heptyl.

In the case of the compound represented by the general formula (I) wherein $R^1$ stands for a hydrogen atom, it can be formed by conventional methods via the salts thereof with various cations such as an alkali metal, for example sodium and potassium, an alkali earth metal, for example, calcium, an inorganic base, for example, ammonia, an organic base, for example, cyclohexylamine, N-methyl-D-glucosamine, or a basic amino acid (lysine, arginine and the like).

The D-phenylalanine derivative as shown by the formula (I) mentioned above, can be prepared by using conventional N-acylating reactions as in the Examples given below.

Most of the phenylalanine derivatives supplied by this invention are novel compounds which have not been described yet in the literature.

The D-phenylalanine derivatives used in the present invention are useful as a hypoglycemic agent for treating diabetic mammals including humans. The derivatives can be used for lowering blood sugar by formulating them into a preparation such as tablets, capsules, and elixirs for oral administration and into an aseptic liquid preparation or an aseptic suspension preparation for parenteral administration such as subcutaneous, intramuscular, intavenous injection, and suppositories. The D-phenylalamine derivatives in the present invention can be administered to a subject necessitating such treatment (animals and humans) in a dosage range of 0.1 to 1,000 mg per subject generally several times a day, that is, in a total daily dosage of 0.2 to 2,000 mg. The dosages varies according to the seriousness of disease, the body weight of subjects, and other factors acknowledged by those skilled in the art.

To produce the preparations using the D-phenylalanine derivatives as described above for the present invention, they may be converted to dosage forms such as tablets, granules, powders, capsules, injections and suppositories by conventional methods.

For the production of oral preparations, there may be added the to the D-phenylalanine derivative as the principal agent, adjuvants such as fillers, binders, disintegrators, lubricants, colors, and correctives, as necessary, and then formed by conventional methods into tablets, coated tablets, granules, powders, capsules and the like.

Examples of specific materials which can be incorporated into tablets, capsules, and so forth are as follows: fillers such as cornstarch, lactose, white sugar, glucose, sorbitol, and crystalline cellulose; binders such as polyvinyl alcohol, polyvinyl ether, ethyl cellulose, methyl cellulose, gum arabic, tragacanth gelatine, shellac, hydroxypropyl cellulose, hydroxypropyl starch, polyvinyl pyrrolidone; disintegrators such as starch, agar, gelatine powder, crystalline cellulose, calcium carbonate, sodium bicarbonate, calcium citrate, dextrin and pectin; lubricants such as magnesium stearate, talc, polyethylene glycol, silica, hardened plant oil; colors such as one which is allowed as an additive for the medicines; correctives such as cocoa powder, mentha herb, aromatic acid, mentha oil, borneol, cinnamon bark powder. These tables and granules may be coated with sugar, gelatine, or the like, as desired.

For the production of the injectable formulations, there may be added to the phenylalanine derivative as the principal agent, a pH adjusting agent, a buffer agent, a stabilizing agent, preservatives or the like, as necessary to produce a material for subcutaneous, intramuscular or intravenous injection by conventional methods.

EXAMPLES

The present invention will be further explained in the following examples.

EXAMPLE 1

N-(4-Ethylbenzoyl)-D-phenylalanine

D-Phenylalaine 2 g (12 mmole) was dissolved in 10% aqueous sodium hydroxide solution (10 ml), and acetone (10 ml) was added. An acetone (5 ml) solution of 4-ethyl benzoyl chloride (2.5 g, 15 mmole) and a 10% aqueous sodium hydroxide solution were added dropwise to the mixture obtained above while stirring and cooling with ice over 20 minutes, the reaction solution being maintained at pH 10. The reaction solution was returned to the room temperature, stirred for 3 hours, and made an acidic with a dilute hydrochloric acid solution to precipitate crystals. The crystals were filtered, washed with water and recrystallized from ethyl acetate to obtain N-(4-ethylbenzoyl)-D-phenylalanine (3.0 g, yield 83%).

m.p. 165.5°-166° C. Specific Rotation $[\alpha]_D^{23}+4.4°$ (C=1, methanol).

EXAMPLES 2 TO 11

For Examples 2 to 8, in the same manner as in Example 1, using the following starting materials, each compound of 50 mmole, the following product compounds were produced. The compounds in Examples 9 to 11 were already known, and therefore were produced in accordance with the following literature references:

Example 9: J. Amer. Chem. Soc., 73, 1644, 1951,
Example 10: Pol. J. Chem., 53, 2239, 1979, and
Example 11: J. Chromatogr., 264, 63, 1983.

| Example No. | Starting Material | Product | Yield (%) | M.P. (°C.) | Specific Rotation |
|---|---|---|---|---|---|
| 2 | D-phenylalanine | N-(4-toldryl)-D-phenylalanine | 83 | 152-155 | $[\alpha]_D^{28}$ +46.2° (C = 0.5, methanol) |
| 3 | D-phenylalanine | N-(2-fluoro-benzoyl)-D-phenylalanine | 74 | 91.5-93.5 | $[\alpha]_D^{19}$ −8.8° (C = 1, methanol) |
| 4 | D-phenylalanine | N-(3-fluoro-benzoyl)-D-phenylalanine | 81 | 112.5-116 | $[\alpha]_D^{22}$ +48.6° (C = 1, methanol) |
| 5 | D-phenylalanine | N-(4-fluoro-benzoyl)-D-phenylalanine | 80 | 142-145 | $[\alpha]_D^{28}$ +40.4° (C = 0.5, methanol) |
| 6 | D-phenylalanine | N-(3-trifluoro-methylbenzoyl)-D-phenylalanine | 77 | 118-119 | $[\alpha]_D^{28}$ +40.4° (C + 1, methanol) |
| 7 | D-phenylalanine | N-(4-trifluoro-methylbenzoyl)-D-phenylalanine | 70 | 136-137.5 | $[\alpha]_D^{28}$ +36.3° (C = 1, methanol) |
| 8 | D-phenylalanine | N-4-anisoyl)-D-phenylalanine | 65 | 85-90 | $[\alpha]_D^{20}$ +60.2° (C = 0.5, methanol) |
| 9 | D-phenylalanine | N-benzoyl-D- | 81 | | |

-continued

| Example No. | Starting Material | Product | Yield (%) | M.P. (°C.) | Specific Rotation |
|---|---|---|---|---|---|
| | | phenylalanine | | | |
| 10 | D-phenylalanine | N-nicotinoyl-D-phenylalanine | 62 | | |
| 11 | D-phenylalanine | N-(2-naphthoyl)-D-phenylalanine | 83 | | |

EXAMPLE 12

N-Cyclopentylcarbonyl-D-phenylalanine

Cyclopentane carboxylic acid (1.5 g, 13 mmole) was dissolved in chloroform (50 ml), and N-hydroxysuccinimide 1.7 g was added. N,N'-Dicyclohexylcarbodiimide (3.0 g) was gradually added to the mixture as obtained above while stirring and cooling with ice, and the mixture was stirred for 1 hour at the same temperature. The mixture was further stirred for 7 hours at room temperature. Glacial acetic acid (2 ml) was added to the mixture, and stirred for 1 hour. The insoluble matter was removed by filtration. The filtrate was washed with saturated aqueous sodium bicarbonate solution (30 ml), 1N aqueous hydrochloric acid solution (30 ml), and water (30 ml), and dried over magnesium sulfate. The magnesium sulfate was removed by filtration, and the solution thus obtained was concentrated under reduced pressure to dryness. The matter was recrystallized from ethyl acetate to afford cyclopentane carboxylic acid N-hydroxysuccinimide ester (2.5 g, yield 91%).

The ester derivative thus obtained above (2.5 g), was dissolved in chloroform (20 ml). This solution was added to a chloroform solution (40 ml) of D-phenylalanine methyl ester hydrochloride (3.0 g, 14 mmole) and triethylamine (1.4 g), and the mixture thus obtained was stirred for 18 hours at room temperature. The reaction solution was washed with 1N aqueous hydrochloric acid solution (40 ml), saturated aqueous sodium bicarbonate solution (40 ml) and water (40 ml), and dried over magnesium sulfate. The magnesium sulfate was removed by filtration and the filtrate was concentrated under reduced pressure to dryness. The matter was recrystallized from ethyl acetate-n-hexane to afford N-cyclopentylcarbonyl-D-phenylalanine methyl ester (3.0 g, yield 84%).

The methyl ester derivative (3.0 g) thus obtained above, was dissolved in methanol (10 ml), and 1N aqueous sodium hydroxide solution (20 ml) was added. The mixture was stirred for 30 minutes at room temperature and then made acidic with an addition of a dilute hydrochloric acid to precipitate crystals. The crystals were filtered, washed with water, and recrystallized from methanol-water to give the desired product (2.7 g, yield 80%).

m.p. 108°–110° C. Specific Rotation $[\alpha]_D^{22}-35.2°$ (C=0.5, methanol).

EXAMPLES 13 TO 18

For Examples 13 to 16, in the same manner as in Example 12, using as the starting material the following compounds, each of 15 mmole, the following products were obtained. The compounds of Examples 17 and 18 stated in the above table were known, and therefore were produced in accordance with the following literature references:

Example 17: BEXXA BELG. NO. 893553, 48, 1981, and

Example 18: Bull. Chem. Soc. Jpn., 57, 2171, 1984.

| Example No. | Starting Material | Product | Yield (%) | M.P. (°C.) | Specific Rotation $[\alpha]_D^{22}$ (C = 0.5, methanol |
|---|---|---|---|---|---|
| 13 | 2-benzofurane carboxylic acid | N-(2-benzofuran-yl-carbonyl)-D-phenylalanine | 59 | 114–116 | +89.6° |
| 14 | 5-indane carboxylic acid | N-(5-indanyl-carbonyl)-D-phenylalanine | 64 | 160–161 | +52.0° |
| 15 | 3-cyclohexene carboxylic acid | N-(3-cyclo-hexenylcarbonyl-) D-phenylalanine | 62 | 100–101 | −12.6° |
| 16 | bicyclo-[2,2,1]heptan-2-ylcarboxylic acid | N-(bicyclo-[2,2,1]heptan-2-ylcarbonyl)-D-phenylalanine | 50 | 179–181 | +33.4° |
| 17 | cyclohexene carboxylic acid | N-cyclohexyl-carbonyl-D-phenylalanine | 65 | | |
| 18 | benzoic acid | N-benzoyl-D-phenylalanine methyl ester | 65 | | |

EXAMPLE 19

N-(4-Isopropylcyclohexylcarbonyl)-D-phenylalanine

Platinum oxide (200 mg) as a catalyst was suspended in acetic acid (20 ml), and then (s)-(−)perillic acid (2 g, 12 mmole) was added. The mixture thus obtained was stirred for 8 hours at room temperature under a current of hydrogen gas. The catalyst was removed by filtration, and the filtrate was concentrated under reduced pressure to a dryness. The matter was recrystallized from methanol-water to obtain 4-isopropyl cyclohexane carboxylic acid (1.9 g, yield 93%).

After that, in the same manner as the reaction in Example 1, N-(4-isopropylcyclohexylcarbonyl)-D-phenylalanine was produced. It was crystallized from methanol-water to give the desired product (2.5 g, yield 61%).

m.p. 230°–232° C. Specific Rotation $[\alpha]_D^{22}-28.2°$ (C=0.5, methanol).

EXAMPLE 20

ICR-CDI mice (Male, five weeks old, Body weight: 20 g) which had been bred for one week, were abstained from food for 18 hours, and then used as test subjects.

The phenylalanine derivative of the present invention was suspended in 0.5% CMC-0.05M tris-hydrochloride buffer (pH 7.4). The sample solution thus obtained was administered orally in fixed amounts to the test subjects. A predetermined time later, the percentage decrease in blood glucose with the comparison to the control group was determined. The results are shown in the following table.

| | Decrease in Blood Glucose (%) | |
|---|---|---|
| Example No. | Amounts used (mg/kg) | 60 Minutes |
| 1 | 25 | 34 |
| 2 | 100 | 32 |
| 3 | 100 | 24 |
| 4 | 100 | 24 |
| 5 | 100 | 43 |
| 6 | 250 | 37 |
| 7 | 100 | 33 |
| 8 | 100 | 38 |
| 9 | 100 | 34 |
| 10 | 250 | 19 |
| 11 | 250 | 17 |
| 12 | 50 | 22 |
| 13 | 100 | 31 |
| 14 | 250 | 28 |
| 15 | 100 | 28 |
| 16 | 250 | 16 |
| 17 | 100 | 27 |
| 18 | 250 | 37 |
| 19 | 25 | 50 |

EXAMPLE 21

N-Cumoyl-D-Phenylalanine

Cumic acid (15.0 g, 91 mmole) was dissolved in chloroform (150 ml), and N-hydroxysuccinimide (11.4 g, 99 mmole) was added thereto. N,N'-Dicyclohexylcarbodiimide (20.4 g, 99 mmole) was added gradually to the mixture obtained above while cooling with ice and stirring, and then the mixture thus obtained was returned to room temperature. The mixture was further stirred for 15 hours at room temperature. Glacial acetic acid (5 ml) was added thereto, and the mixture thus obtained was stirred and the insoluble matter was removed by filtration. The filtrate was washed with saturated aqueous sodium bicarbonate (300 ml) and water (300 ml), and dried over magnesium sulfate. The magnesium sulfate was removed by filtration, and the filtrate thus obtained was concentrated under reduced pressure to dryness. The resultant substance was recrystallized from ethyl acetate to obtain cumic acid N-hydroxysuccinimide ester (18.8 g, yield 72 mmole).

The ester thus obtained above (18.8 g) was added to the chloroform solution (150 ml) of D-phenylalanine methyl ester hydrochloride (23.0 l g, 110 mmole) and triethylamine (10.8 g, 110 mmole), and the mixture thus obtained was stirred for 15 hours at room temperature. The reaction solution was washed with 1N aqueous hydrochloric acid solution (300 ml), saturated aqueous sodium bicarbonate (300 ml) and water (300ml) and dried over magnesium sulfate. The magnesium sulfate thus used was removed by filtration, and the filtrate thus obtained was concentrated under reduced pressure to dryness.

The residue thus obtained was recrystallized from ethyl acetate-n-hexane to obtain N-cumoyl-D-phenylalanine methyl ester (20.5 g, yield 69%).

The methyl ester thus obtained above (20.5 g) was dissolved in methanol (100 ml), and then 1N aqueous sodium hydroxide (100 ml) was added thereto. The mixture thus obtained was stirred for 10 minutes at room temperature, and was made acidic with an addition of diluted aqueous hydrochloric acid solution to precipitate crystals. The crystals were filtered, washed with water and recrystallized from methanol-water to give the desired product (18.1 g, yield 64%).

m.p. 177°–178° C. Specific Rotation $[\alpha]_D^{20}+25.5°$ (C=1, methanol).

EXAMPLES 22 to 30

In the same manner as in Example 21, using as the starting material the following compounds, each at 50 mmole, the following product compounds were produced.

| Example No. | Starting Material | Product | Yield (%) | M.P. (°C.) | Specific Rotation |
|---|---|---|---|---|---|
| | | | | | $[\alpha]_D^{20}$ (C = 1, methanol) |
| 22 | (s)-perillic acid | N-[(s)-perilloyl]-D-phenylalinine | 44 | 109–110 | −37.2° |
| 23 | trans-4-n-propylcyclo-hexane carboxylic acid | N-(trans-4-n-propylcyclo-hexylcarbonyl)-D-phenylalanine | 48 | 104–105 | −8.8° |
| 24 | trans-4-n-butylcyclo-hexane carboxylic acid | N-(trans-4-n-butylcyclohexyl-carbonyl)-D-phenylalanine | 50 | 144–145 | −7.5° |
| 25 | 4-tert-butyl-benzoic acid | N-(4-t-butyl-benzoyl)-D-phenylalanine | 55 | 177–178 | +51.5° |
| 26 | cuminic acid | N-cumoyl-L-phenylalanine | 63 | 121–123 | $[\alpha]_D^{23}$ −29.3° (C = 1, methanol) |
| 27 | cyclopentane carboxylic acid | N-cyclopentyl-carbonyl-L-phenylalanine | 40 | 115–117 | $[\alpha]_D^{23}$ −30.1° (C = 1, methanol) |
| 28 | trans-4-methyl-cyclo- | N-(trans-4-methylcyclohexyl- | 43 | 124–125 | $[\alpha]_D^{23}$ −11.5° (C = 1, methanol) |

-continued

| Example No. | Starting Material | Product | Yield (%) | M.P. (°C.) | Specific Rotation |
|---|---|---|---|---|---|
| | hexane carboxylic acid | carbonyl)-D-phenylalanine | | | |
| 29 | trans-4-ethylcyclohexane carboxylic acid | N-(trans-4-ethylcyclohexyl-carbonyl)-D-phenylalanine | 53 | 96–97 | $[\alpha]_D^{23}$ −11.1° (C = 1, methanol) |
| 30 | trans-4-t-butyl-cyclohexane carboxylic acid | N-(trans-4-t-butylcyclohexylcarbonyl)-D-phenylalanine | 49 | 160–161 | $[\alpha]_D^{23}$ −9.0° (C = 1, methanol) |

EXAMPLE 31

N-(trans-4-isopropylcyclohexylcarbonyl)-D-phenylalanine

Platinum oxide (500 mg) as a catalyst was suspended in acetic acid (50 ml) and cumic acid (10 g, 61 mmole) was added thereto. The mixture thus obtained was stirred vigorously for 2 hours at room temperature under a pressure of hydrogen 5 kg/cm$^2$. The catalyst was removed by filtration, and the filtrate was concentrated under reduced pressure to a solid state. The resultant substance was distilled under reduced pressure of 1 mmHg ($1.3\times10^{-3}$ kg/cm$^2$), at 113°–116° C. to obtain 4-isopropylcyclohexane carboxylic acid yielding 10 g (96%) in a ratio of 3 parts of cis-form per 1 part of trans-form by weight.

To methanol (70 ml) at less than −20° C., thionyl chloride (17 ml) was added dropwise, and the carboxylic acid (10 g) as obtained above was added. The mixture thus obtained was stirred for 15 hours at room temperature, and then concentrated under reduced pressure to a solid substance. The substance thus obtained was distilled under reduced pressure of 0.7 mmHg ($9.2\times10^{-4}$ kg/cm$^2$) at 66° C. to obtain 4-isopropylcyclohexane carboxylic acid methyl ester (9.5 g, yield 88%).

To the methyl ester (b 9.5 g) thus obtained, sodium hydride (120 mg) was added, and the mixture was heated at 150° C. for 2 hours under a current of nitrogen gas. The reaction solution was cooled and then subjected to a reduced pressure distillation of 0.7 mmHG ($9.2\times10^{-4}$ kg/cm$^2$) at 66° C. to obtain 4-isopropylcyclohexane carboxylic acid methyl ester in a ratio of 6 parts trans-form per 1 part cis-form.

The methyl ester (9.0 g) thus obtained was dissolved in methanol (50 ml), and 1N aqueous sodium hydroxide solution (50 ml) was added thereto. The mixture thus obtained was stirred for 10 minutes at room temperature and made acidic with an addition of a dilute aqueous hydrochloric acid solution to precipitate crystals. The crystals were filtered, washed with water, and crystallized from methanol-water to give trans-4-isopropylcyclohexane carboxylic acid (6.8 g, yield 78%).

After that, in the same manner as in Example 21, using as a starting material the carboxylic acid derivative (6.8 g, 40 mmole), N-(trans-4-isopropylcyclohexylcarbonyl)-D-phenylalanine was produced, and recrystallized from methanol-water to give the desired product (8.2 g, yield 65%).

m.p. 129°–130° C. Specific Rotation $[\alpha]_D^{20}$−9.4° (C=1, methanol).

EXAMPLES 32 TO 35

In the same manner as in Example 26, using as the starting material the following compounds, each of 40 mmole, the following product compounds were produced.

| Example No. | Starting Material | Product | Yield (%) | M.P. (°C.) | Specific Rotation $[\alpha]_D^{20}$ (C = 1, methanol) |
|---|---|---|---|---|---|
| 32 | trans-4-isopropylcyclohexane carboxylic acid | 4-(trans-4-isopropylcyclohexylcarbonyl)-D-phenylalanine methyl ester | 52 | 137–138 | +8.8° |
| 33 | trans-4-isopropylcyolohexane carboxylic acid | N-(trans-4-isopropylcyclohexylcarbonyl)-L-phenylalanine | 56 | 130–131 | +9.5° |
| 34 | trans-4-isopropylcyclohexane carboxylic acid | N-(trans-4-isopropylcyclohexylcarbonyl)-2-phenylethylamine | 66 | 134—135 | — |
| 35 | trans-4-isopropylcyclohexane carboxylic acid | N-(trans-4-isopropylcyclohexylcarbonyl)-D-phenylalanine benzylester | 58 | 129—130.5 | +8.4° |

EXAMPLE 26

N-(Cis-4-isopropylcyclohexylcarbonyl)-D-phenylalanine

4-Isopropylcyclohexane carboxylic acid methyl ester (9.5 g) (Cis-form:trans-form=3:1) was obtained in the same manner as in Example 26. Cis-4-isopropylcyclohexane carboxylic acid methyl ester (7 g) was obtained from the product thus obtained by a high performance liquid chromatography of YMC A-043 column using as the solvent a mixture of n-hexane and 1,2-dichloro ethane in a ratio of 75:25.

After that, in the same manner as in Example 21, using as a starting material the cis-form thus obtained (6.5 g, 38 mmole), N-(Cis-4-isopropylcyclohexylcarbonyl)-D-phenylalanine was produced, and recrystallized from methanol-water to give the desired product (8 g, yield 66%).

m.p. 111°–112° C. Specific Rotation $[\alpha]_D^{20}$ −13.2° (C=1, methanol).

EXAMPLE 37

ICR-CDI mice (Male, five weeks old, Body weight: 20 g) were abstained from food for 18 hours, and then used as test subjects.

The phenylalanine derivative of the present invention was suspended in 0.5% CMC-0.14M sodium chloride buffer solution (pH 7.4). The solution thus obtained was administered orally in fixed volume amounts to the test subjects. After a predetermined time, the percentage decrease of the blood glucose against the control group was determined. The results are shown in the following Table.

| Example No. | Amounts used in sample mg/kg body weight | Decrease in blood glucose after 60 minutes (%) |
|---|---|---|
| 21 | 25 | 26 |
| 22 | 100 | 43 |
| 23 | 100 | 35 |
| 24 | 100 | 30 |
| 25 | 100 | 32 |
| 26 | 100 | 0 |
| 27 | 100 | 0 |
| 28 | 6.25 | 24 |
| 29 | 6.25 | 31 |
| 30 | 6.25 | 30 |
| 31 | 1.5 | 30 |
| 32 | 6.25 | 37 |
| 33 | 100 | 23 |
| 34 | 100 | 14 |
| 35 | 25 | 24 |
| 36 | 100 | 27 |

It is clear from the foregoing that the D-phenylalanine derivatives as described above can be used as an antidiabetic drug for oral administration as well as the more usual parenteral administration.

We claim:

1. A D-phenylalanine derivative of the formula $$R^4—CO—NR^3—CH(COOR^1)—CH_2—C_6H_5$$

or a salt thereof or a precursor which can be converted into said D-phenylalanine derivative in vivo, wherein:

$R^1$ is hydrogen or $C_{1-5}$ alkyl,

Ris hydrogen or $C_{1-5}$ alkyl; and $R^4$ is cyclohexane substituted at the 4- or 5-position by methyl, ethyl, ispropyl, tert-butyl, ethene, or isopropene or cyclohexene substituted at the 4- or 5-position by methyl, ethyl, isopropyl, tert-butyl, ethene, or isopropene.

2. The D-phenylalanine derivative of claim 1, wherein $R^4$ is said substituted cyclohexane.

3. The D-phenylalanine derivative of claim 1, wherein $R^4$ is said substituted cyclohexane.

4. The D-phenylalanine derivative of claim 1, wherein the said derivative is N-(4-isopropylcyclohexylcarbonyl)-D-phenylalanine.

5. The D-phenylalanine derivative of claim 1, wherein the said derivative is N-(4-isopropylcyclohexylcarbonyl)-D-phenylalanine: N-[(S)-perilloyl]-D-phenylalanine; N-(4-methylcyclohexylcarbonyl)-D-phenylalanine; N-(4-ethylcyclohexylcarbonyl)-D-phenylalanine; or N-(4-t-butylcyclohexylcarbonyl)-D-phenylalanine.

6. The D-phenylalanine derivative of claim 1, wherein the said derivative is N-[(s)-perilloyl]-D-phenylalanine; N-(trans-4-methylcyclohexylcarbonyl)-D-phenylalanine; N-(trans-4-ethylcyclohexylcarbonyl)-D-phenylalanine; N-(trans-4-isopropylcyclohexylcarbonyl)-D-phenylalanine; or N-(trans-4-t-butylcyclohexylcarbonyl)-D-phenylalanine.

7. The D-phenylalanine derivative of claim 1, wherein $R^1$ is hydrogen and $R^3$ is hydrogen.

8. The D-phenylalanine derivative of claim 1, wherein $R^4$ is perilloyl.

9. The D-phenylalanine derivative of claim 1, wherein said substituted cyclohexane is substituted at the 4-position.

10. The D-phenylalanine derivative of claim 1, wherein said substituted cyclohexane is substituted at the 5-position.

11. The D-phenylalanine derivative of claim 1, wherein said substituted cyclohexene is substituted at the 4-position.

12. The D-phenylalanine derivative of claim 1, wherein said substituted cyclohexene is substituted at the 5-position.

13. The D-phenylalanine derivative of claim 1, wherein said substituted cyclohexane or said substituted cyclohexene is substituted with methyl, ethyl, isopropyl or tert-butyl.

14. The D-phenylalanine derivative of claim 1, wherein said substituted cyclohexane or said substituted cyclohexene is substituted by ethene, or isopropene.

15. A pharmaceutical composition, comprising a D-phenylalanine derivative of claim 1 and a pharmaceutical excipient.

*16. The compound N-(trans-4-isopropylcyclohexylcarbonyl)-D-phenylalanine.*

* * * * *

UNITED STATES PATENT AND TRADEMARK OFFICE

CERTIFICATE OF CORRECTION

PATENT NO. : RE34878

DATED : March 14, 1995

INVENTOR(S) : Shigeshi TOYOSHIMA, et al.

It is certified that error appears in the above-indentified patent and that said Letters Patent is hereby corrected as shown below:

On the title page, Item [62], the Related U.S. Application Data should read:

--Division of Ser. No. 844,970, Mar. 27, 1986, abandoned.--

Signed and Sealed this

Thirtieth Day of May, 1995

*Attest:*

Bruce Lehman

BRUCE LEHMAN

*Attesting Officer*

*Commissioner of Patents and Trademarks*